United States Patent [19]
Guhl

[11] Patent Number: 5,063,918
[45] Date of Patent: Nov. 12, 1991

[54] MULTI-MODE DISTRACTION SYSTEM FOR ANKLE ARTHROSCOPY

[76] Inventor: James F. Guhl, 13455 Elmhurst Dr. Pky., Elm Grove, Wis. 53122

[21] Appl. No.: 523,132

[22] Filed: May 14, 1990

[51] Int. Cl.$^5$ ............................ A61F 5/04; A61F 5/37; A61F 13/00
[52] U.S. Cl. .................................... 128/84 R; 128/75; 606/53; 606/57; 606/105; 269/328
[58] Field of Search ................. 606/57, 58, 86, 90, 606/53, 54, 105; 128/80 R, 845, 882, 75, 83, 84 R; 269/328

[56] References Cited

U.S. PATENT DOCUMENTS

| | | | |
|---|---|---|---|
| 743,663 | 11/1903 | Scheidl | 128/84 R |
| 1,863,188 | 6/1932 | Clash | 606/57 X |
| 1,869,726 | 8/1932 | Youngren | 606/57 |
| 1,928,658 | 10/1933 | Anderson | 128/83 |
| 1,950,948 | 3/1934 | Murray | 128/75 |
| 1,997,466 | 4/1935 | Longfellow | 606/57 X |
| 2,034,680 | 3/1936 | Longfellow | 128/83 X |
| 2,110,414 | 3/1938 | Bell | 128/84 R |
| 2,198,995 | 4/1940 | Gray | 128/84 R |
| 2,204,266 | 6/1940 | Wilcox | 128/84 R |
| 2,238,870 | 4/1941 | Haynes | 128/84 R |
| 2,978,713 | 4/1961 | Scalzitti et al. | 128/845 X |
| 3,020,909 | 2/1962 | Stevens | 128/84 R |
| 3,135,257 | 6/1964 | Anderson | 128/84 R |
| 3,547,113 | 12/1970 | Swanson | 606/57 X |
| 4,323,080 | 4/1982 | Melhart | 269/328 X |
| 4,428,571 | 1/1984 | Sugarman | 269/328 |
| 4,443,005 | 4/1984 | Sugarman et al. | 269/328 |
| 4,526,355 | 7/1985 | Moore et al. | 269/328 |
| 4,549,540 | 10/1985 | Caspari et al. | 128/882 |
| 4,573,482 | 3/1986 | Williams, Jr. | 128/845 |
| 4,615,516 | 10/1986 | Stulberg et al. | 128/80 R |
| 4,624,458 | 11/1986 | Fendrik | 128/75 X |
| 4,766,891 | 8/1988 | Schultz | 128/80 R X |
| 4,848,368 | 7/1989 | Kronner | 606/57 |
| 4,886,258 | 12/1989 | Scott | 269/328 |
| 4,968,316 | 11/1990 | Hergenroeder | 606/90 |
| 5,025,802 | 6/1991 | Laico et al. | 128/75 X |

Primary Examiner—Robert Bahr
Assistant Examiner—Linda C. M. Dvorak
Attorney, Agent, or Firm—Andrus, Sceales, Starke & Sawall

[57] ABSTRACT

A system and related method for ankle arthroscopy distraction includes both non-invasive external and invasive skeletal distractors which may be individually applied in a serial manner to provide ever increasing distraction forces as may be dictated by the required arthroscopic procedure. The angle of the distracted ankle may be selectively varied at anytime during any of the non-invasive or invasive distraction techniques without the need to halt the procedure, thereby obviating the need to reprep or to reposition or redrape the patient. The non-invasive distractor is of relatively simple and compact construction and is easily repositionable with changes in the angle of the ankle to allow ready and complete access for all surgical procedures. The skeletal distractors utilize all of the beneficial features of prior art devices and incorporate the additional beneficial feature of two types of pins of varying design and distraction load carrying capacity which may be applied in either a unilateral or bilateral manner to provide a wide range of distraction capability. An adjustable leg holder allows a wide range of angular positioning of the lower leg and ankle during application of any of the distraction techniques.

17 Claims, 3 Drawing Sheets

MULTI-MODE DISTRACTION SYSTEM FOR ANKLE ARTHROSCOPY

BACKGROUND OF THE INVENTION

The present invention relates to methods and apparatus useful in the performance of ankle arthroscopy procedures and, more particularly, to a multifunctional system for providing ankle joint distraction in support of arthroscopic procedures.

In order to provide sufficient space for the arthroscope and various types of surgical instruments used in ankle arthroscopy, it is usually necessary to provide some form of joint distraction. The degree of distraction will vary depending on the nature of the procedure and the type and size of surgical instruments required. Various methods of non-invasive and invasive (skeletal) distraction have been utilized.

In general, non-invasive distraction methods are limited in the maximum amount of ankle joint distraction they can provide, but are basically less complex to utilize. Invasive distraction methods, on the other hand, can provide a much higher level of ankle joint distraction, but are inherently more complex to perform and, therefore, generally involve somewhat greater risk of complications. Nevertheless, invasive distraction may be the only appropriate means which can be utilized to accommodate the required arthroscopic procedure.

All non-invasive distraction techniques utilize some method of applying a distally directed force or load on the foot and ankle axially of the lower leg in opposition to an oppositely directed anchoring force applied through the leg. The distraction force may be applied by gravity, manually by a surgical assistant, or by some device providing a mechanical advantage. The distraction force may be controlled or relatively uncontrolled. Invasive skeletal distraction is typically applied by a mechanical distractor which is attached across the ankle joint to generally horizontally disposed pins in the lower tibia and heel bone. The distractor is threaded such that it is extensible against the resistance of the pinned connections to impose a separating tensile force on the ankle joint resulting in the desired distraction. The distractor typically includes a calibrated extensiometer to indicate the amount of distraction force. Bilateral distraction may also be utilized by extending the pins bicortically through the bones and attaching somewhat similar mechanical distractors to each side.

In accordance with prior art techniques, the surgeon would choose a distraction technique believed to be suitable prior to commencement of the surgery. The technique would either be one of several non-invasive methods or some variation on the basic invasive skeletal distraction method. Obviously, if adequate, one of the non-invasive techniques would be preferable to obviate the need for surgical pin placement and the possible complications attendant thereto. Unfortunately, the amount of distraction obtained is often not determinable until the arthroscopic procedure has been commenced and, if adequate distraction by non-invasive methods cannot be attained, the surgical procedure must often be terminated completely.

It would be desirable, therefore, to have an ankle distraction system which could utilize, as necessary, basic non-invasive techniques and, if necessary as the anthroscopic examination or surgical procedure evolves, the direct replacement of non-invasive techniques with a skeletal distraction method or methods to provide a greater amount of distraction. It would also be desirable to have a system in which the preliminary non-invasive distraction could be better monitored and controlled, both in terms of the distraction force applied to the joint and the position at which the ankle is held during the procedure. Similarly, if the need to convert to invasive distraction techniques arises, the system should provide the capability of rapidly converting to an invasive method which provides the amount of distraction needed and allows the ankle to be placed and held in an optimum position for the required surgical technique. In addition, regardless of which technique or method is utilized, the system should be flexible enough to allow repositioning of the limb and the joint during the surgical procedure to provide optimum access to all of the available surgical entrant sites.

SUMMARY OF THE INVENTION

In accordance with the present invention, a unique system and related method are provided for ankle joint distraction which allow varying amounts of distraction to be provided by alternate non-invasive and invasive means, each of which may be utilized with variable ankle positioning. The system provides the surgeon with the ability to quickly switch between several alternate modes as the need for greater distraction or additional time to perform the surgical procedure arises.

The system includes an appropriate means for supporting the patient in a generally supine position and for adjustably supporting the patient's leg posteriorly of the knee joint in a manner to maintain the leg in a flexed position between slightly flexed and acutely flexed. The system includes non-invasive distraction means which are attached by opposite ends to the foot of the patient and the patient support means to provide a selectively variable tensile force on the ankle joint which is sufficient to provide an initial level of ankle joint distraction.

The system also includes skeletal distraction means which includes a proximal end adapted to be pinned to the lower tibia and a distal end adapted to be pinned to the heel bone to provide a selectively variable tensile force on the ankle joint sufficient, if necessary, to provide a greater level of ankle joint distraction force than the non-invasive means. The system also permits progression to heavy bilateral skeletal distraction, if required.

The non-invasive distraction means preferably includes a rigid elongate body having an axially adjustable length and a suitable adjustment means which is operatively attached to the body for manually changing the length thereof. The body is provided with connection means on each end for connecting one end to the patient's foot and the opposite end to the patient support means. The adjustment means is operable to shorten the length of the distractor body between the first and second end connections, thereby imposing a tensile force on the lower leg against the anchoring force of the leg held in the adjustable leg supporting means, to provide the initial level of joint distraction force. Suitable first indicating means are preferably provided on the body of the non-invasive distractor to show the magnitude of the applied tensile force. The first distractor is attached to the foot of the patient by utilizing a foot strap which is demountably attachable to the foot, as with the use of combined foot and heel straps or the like. The connector at one end of the first distractor is attached to the foot strap.

The first skeletal distraction means preferably includes a first unilaterally attachable distractor of a type known in the art which has pin-supporting heads on its proximal and distal ends. In accordance with the present invention, each of the pin-supporting heads is adapted to individually support a large diameter pin and a small diameter pin to allow the distractor to be adapted for either relatively light or heavier skeletal distraction. The large diameter pins are preferably threaded and small diameter pins smooth.

The first distractor is also preferably provided with an indicating means to show the magnitude of the tensile force being applied generally in the range of 35-80 pounds. This system also utilizes a second unilaterally attachable distractor which is adapted to be attached to the other side of the ankle joint opposite the first skeletal distractor. When utilizing both the first and second skeletal distractors, both the proximal and distal pins are inserted bicortically through the respective leg and calcaneous bones and the distractors are attached to opposite ends of the pins.

When the skeletal distraction means are utilized, a foot supporting means may also be used to provide supplemental support for the foot and ankle. The supplemental ankle supporting means includes a foot piece and a holder arm which has a universally pivotal connection at one end attached to the foot piece and a pivotal connection at the other end which is attached to the patient supporting means. The patient supporting means preferably comprises a conventional operating table having a Clark rail attached to one edge thereof, including a conventional Clark rail clamp attached over sterile drapes and to which the pivotal connection at the end of the holder arm may be adjustably attached.

The leg supporting means for adjustably supporting the leg at the knee joint may conveniently comprise a conventional gynecological or urological leg holder. Vertical adjustment of the leg holder can be utilized to vary the flexed position of the leg between the positions of slightly flexed and acutely flexed. The leg holder may also be pivoted in either the horizontal or vertical plane to further adjust the knee support. Adjustment of the leg support may be effected by utilizing conventional clamping attachment to the same Clark rail used to attach and position the non-invasive distractor and the optional ankle holder.

The method of the present invention for providing ankle joint distraction includes the steps of (1) supporting the patient in a generally supine position; (2) adjustably positioning the leg of the patient in a selected position between slightly flexed and acutely flexed by utilizing support beneath the knee joint; (3) applying a first selectively variable tensile force on the ankle joint sufficient to provide an initial level of joint distraction by the external application of a load on the foot of the patient generally axially of the lower leg and against the resistance provided by the knee support; (4) determining the sufficiency of the initial level of distraction; and (5) applying, as necessary, the second selectively variable tensile force on the ankle joint sufficient to provide a greater level of joint distraction force by skeletally applying a unilateral load between proximal and distal pinned connections in the lower tibia and heel bone, respectively. Optionally, the foot may be adjustably supported during application of the second variable tensile force.

If necessary, the method may include the step of applying a supplemental second tensile force on the ankle joint by (1) extending the pinned connections bicortically to the opposite side of the ankle joint, and (2) skeletally applying a supplemental load between the extended pin connections concurrently with application of the initial unilateral compressive load. The method also includes the step of continuously monitoring the externally applied load and, if used, the skeletally applied unilateral load.

BRIEF DESCRIPTION OF THE DRAWINGS

FIG. 2 is an enlarged top plan view of the distraction shown in FIG. 1.

FIG. 7 is a side elevation of the first skeletal distractor shown in FIG. 4.

DETAILED DESCRIPTION OF THE PREFERRED EMBODIMENT

The construction and method of utilizing the system of the present invention will be described together.

Figure 1:
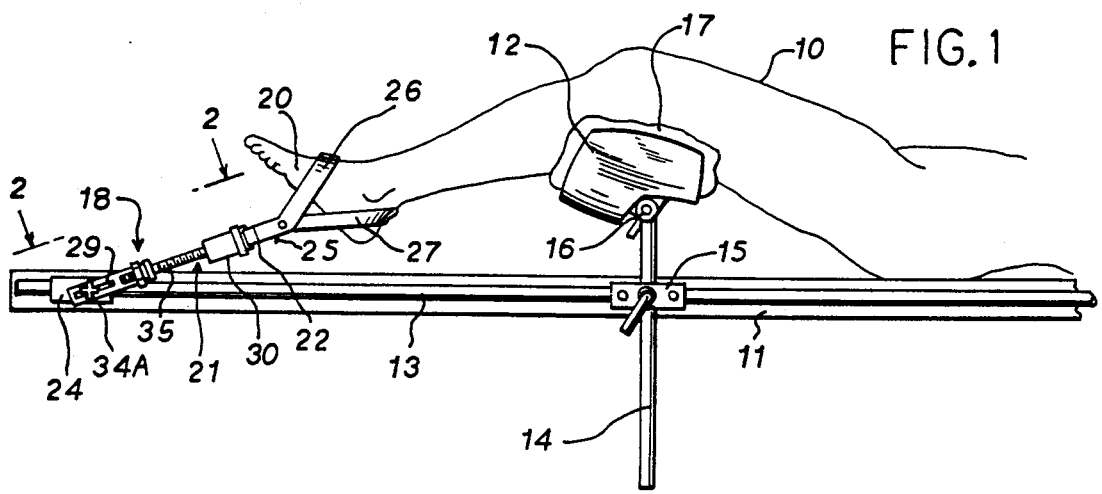
FIG. 1 is a side elevation showing the leg support and non-invasive distractor of the present invention attached to a patient with the leg in the slightly flexed position.

In arthroscopic procedures involving the ankle, where joint distraction is necessary, it is preferable to provide the distraction by a non-invasive technique. A principal advantage of non-invasive distraction is the elimination of the risk of bone infection and stress risers. Non-invasive techniques may be utilized to provide adequate distraction where the patient has a relatively loose ankle joint, for diagnostic ankle arthroscopy, for short surgical procedures, or where there is an easily accessible pathology. Referring to FIG. 1, the system and related method are applied with the patient lying supine on an operating table 11 with the leg 10 supported at the back of the knee vertically above the table 11. Leg support may be conveniently provided by a conventional gynecological or urological leg holder 12 attached in a known manner to a conventional Clark rail 13 attached to and running horizontally along one edge of the operating table 11. The leg holder 12 includes a support arm 14 adjustably attached to the Clark rail 13 by a clamp 15 which allows the assembly to be slid along the rail, pivoted in a horizontal plane, and moved vertically up or down. The upper end of the support arm 14 is connected to the leg holder with a pivot mechanism 16 allowing the holder to be adjustably pivoted in either a horizontal or vertical plane. The construction of the leg holder 12 and support arm 14 are conventional. The leg holder is generously padded with a heavy foam rubber padding 17 to provide as much cushioning as is practicable.

For ankle procedures requiring only anterior access to the joint, the leg 10 may be supported in the slightly flexed position shown in FIG. 1. However, the knee may be flexed over a wide range by suitable vertical adjustment of the support arm 14 in the Clark rail clamp 15.

Figure 3:
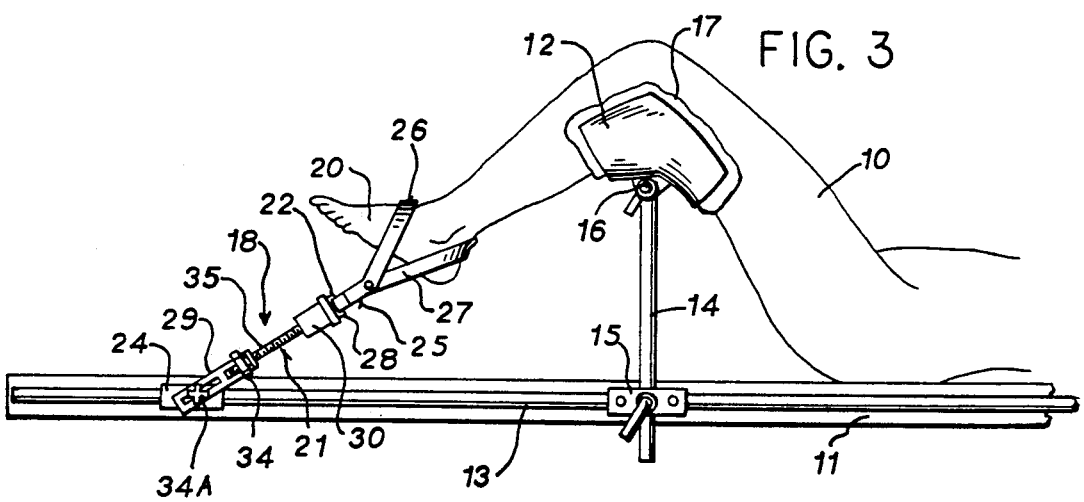
FIG. 3 is a side elevation similar to FIG. 1 showing the leg in the acutely flexed position.
Figure 6:
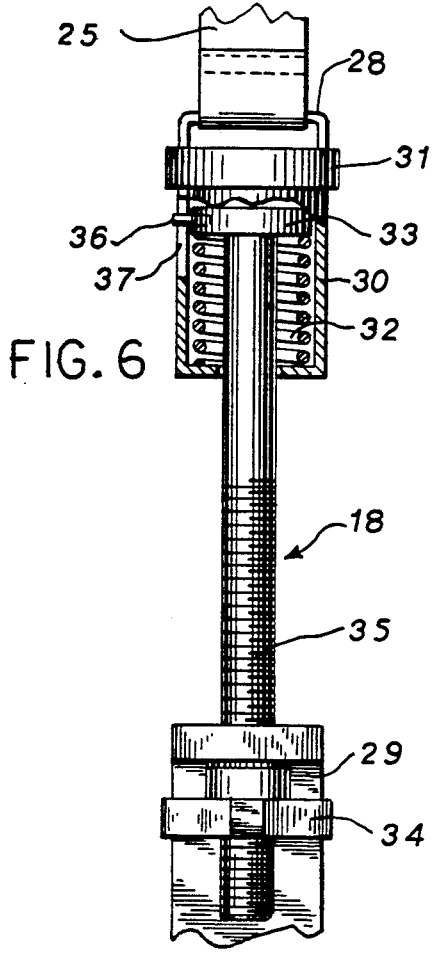
FIG. 6 is a side elevation of the noninvasive distractor shown in FIGS. 1-3.
Figure 8:
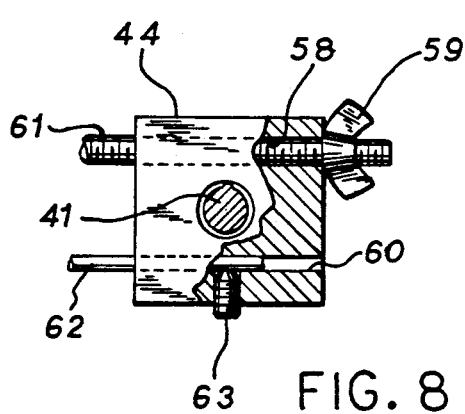
FIG. 8 is an end view of the proximal end of the skeletal distractor taken on line 8—8 of in FIG. 7.

The non-invasive distractor 18 is attached at one end to the foot 20 of the patient and at the other end to the Clark rail 13. Referring also to FIGS. 2, 3 and 6, the non-invasive distractor 18 includes a long rigid body portion 21 having a first connection 22 on its proximal end to the foot 20 and a second connection 23 on its distal end to another clamp 24 adjustably attached to the Clark rail 13 over sterile drapes. Actual attachment of the first connection 22 to the foot is preferably effected with a foot strap assembly 25 attached to the foot with a foot strap 26 and heel strap 27. The first connection 22 preferably comprises a ring 28 attached to the proximal end of the distraction body portion 21 through which the end of the strap assembly 25 is secured. The body portion 21 of the non-invasive distractor 18 includes a tubular end member 30 which is closed at its proximal end by an annular end cap 31. The end cap has the strap attachment ring 28 fixed to its outer face. An adjustment screw 35 is slidably received in the tubular end member 30 and includes an annular bias plate 33 attached to its free proximal end. A coil spring 32 is captured between the bias plate 33 and the inside of distal end of tubular end member 30 and held in a substantially relaxed condition. The distal end of the adjustment screw 35 is threaded and extends freely through an opening in one leg of an L-shaped mounting bracket 29. A threaded adjustment ring 34 is attached to the threaded end of the screw 35. The other leg of the mounting bracket 29 is slotted and is attached to the adjustment knob 34A of Clark rail clamp 24. Manual rotation of adjustment ring 34 effects adjustment of the overall length of distractor 18. Adjustment of the slotted leg of the mounting bracket 29 with the adjustment knob 34A may be utilized for coarse preliminary adjustments.

With the patient positioned as shown in FIG. 1 with the leg in the leg holder 12, the non-invasive distractor 18 is attached to the patient by placing the foot 20 in the foot strap 25. The position of the clamp 24 on the opposite end of the distractor is established by repositioning it along the Clark rail 13 over sterile drapes and adjusting the position of the slotted leg of bracket 29 such that the body portion 21 is approximately axially aligned with the lower leg of the patient. The adjustment ring 34 is then turned by hand to cause an overall shortening of the length of the distractor, thereby imposing a tensile force on the ankle joint resulting in the desired distraction thereof.

As the body portion 21 of the non-invasive distractor 18 is shortened by turning the adjustment ring 34, the resistance to movement will cause the coil spring 32 to be compressed axially. An indicating pin 36 is attached to the adjustment screw 35 and extends radially outwardly through a slot 37 in the tubular end member 30 to move therein as the coil spring is compressed. One edge of the slot 37 is provided with calibrated indications to display a measurement of the distraction force, preferably in pounds.

Non-invasive distraction of the type provided by the distractor 18 described hereinabove must be limited both in terms of the magnitude of the applied force and the duration of the application in order to avoid neurovascular damage. Thus, the maximum force must generally be limited to about 25 pounds and the distraction not maintained for more than 45-50 minutes. However, the amount of distraction obtained with 25 pounds tensile force on the joint may often be inadequate for the required surgical procedure. Furthermore, the procedure may require a longer duration than the allowable 45-50 minute maximum. In addition, the position of the leg and ankle in FIG. 1 make access to the posterior arthroscopic portals difficult or impossible.

The latter problem may be alleviated by repositioning the leg to the acutely flexed position shown in FIG. 3 and simultaneously repositioning the non-invasive distractor 18 to accommodate the new leg position. The position of increased leg flection is provided by extending the support arm 14 on the leg holder 12 via the Clark rail clamp 15. The clamp 24 securing the distractor 18 is also repositioned by repositioning the same along the Clark rail 13 over sterile drapes until the distractor is again disposed generally in axial alignment with the lower leg. This repositioning may be done anytime during the surgical procedure when, for example, need for posterior access to the ankle joint arises. Again, however, as with the FIG. i position, the maximum distraction force and the duration of distraction are limited.

An important aspect of the system of the present invention is the ability to rapidly convert from the non-invasive distraction previously described and shown in FIGS. 1 and 3 to skeletal distraction, if needed. Thus, if it is found during an arthroscopic procedure that the amount of distraction is inadequate for the instruments or the required procedure, or if the anticipated time for the procedure is unexpectedly lengthened, conversion to skeletal distraction can readily be effected without reprepping and without repositioning or redraping the patient.

Figure 4:
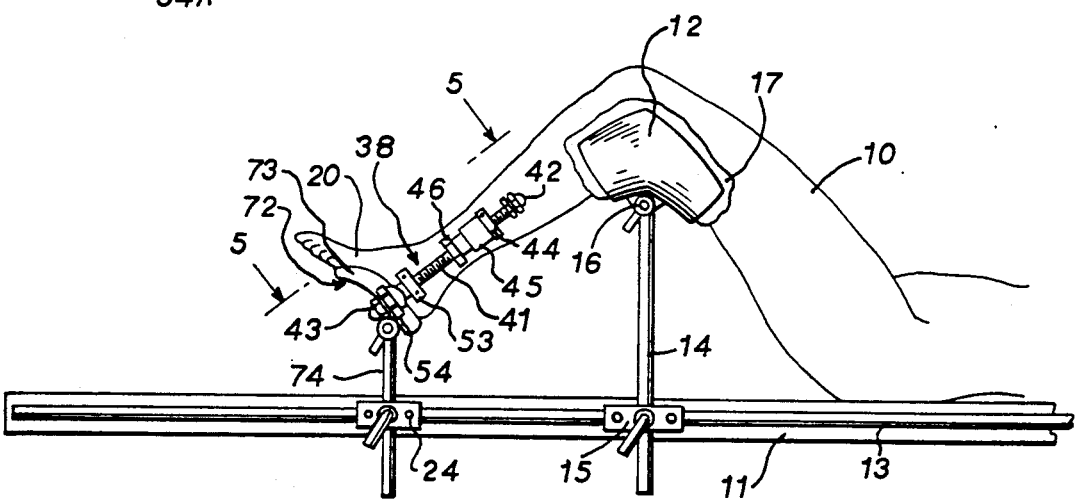
FIG. 4 is a side elevation similar to FIG. 3 showing the attachment of a skeletal distractor and additionally showing the use of an optional foot support.
Figure 5:
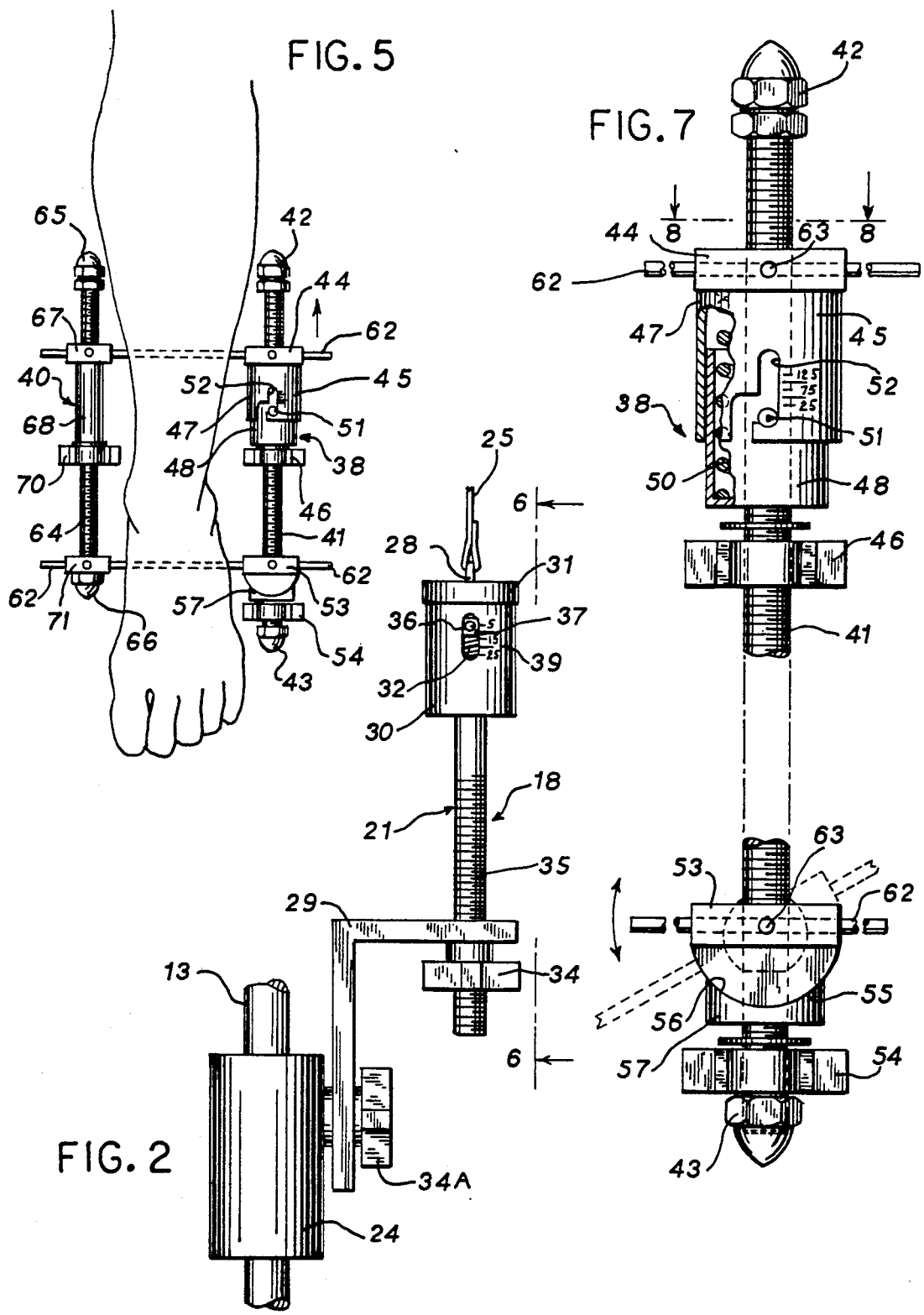
FIG. 5 is a frontal elevation of the lower leg of a patient showing the attachment of two distractors in a bicortical mode utilizing common pinned connections.

Referring to FIGS. 4 and 5, skeletal distraction is effected by utilizing a single skeletal distractor 38 (FIG. 4) or a double distractor arrangement (FIG. 5) in which a second skeletal distractor 40 is simultaneously attached across the ankle joint. Each of the distractors is adapted to be pinned to the lower tibia of the patient's leg and to the heel bone of the foot, and then mechanically extended to provide a selectively variable tensile force on the ankle joint sufficient to produce the necessary distraction.

Referring also to FIG. 7, the first skeletal distractor 38 includes a threaded through shaft 41 extending the full length of the distractor. A pair of stop nuts 42 and 43 are attached to the proximal and distal ends, respectively, of the threaded shaft 41. A proximal head 44 is slidably mounted on the shaft 41 to slide freely therealong. An extensiometer 45, similar to indicator 39 on the non-invasive distractor 18, is attached to the proximal head for movement therewith along the shaft 41. A proximal wing nut 46 is threaded on the shaft 41 and may be turned to adjust the position of the integral head 44 and extensiometer 45 along the shaft. The extensiometer 45 includes an outer sleeve 47 and an inner sleeve 48 which is telescoped axially into the outer sleeve. A coil spring 50 is positioned between the proximal end of the inner sleeve 48 and the inside face of the proximal head 44 to capture the spring 50 in its relaxed state therebetween. An indicating pin 51 is attached to the inner sleeve 48 and extends radially outwardly into a slot 52 in the outer sleeve 47. As with indicator 39, the slot 52 includes indicia calibrated in pounds to provide an indication of the amount of distraction force as will be described hereinafter. A distal head 53 is attached to the opposite end of the shaft 41 in a manner such that it is journaled for rotation thereon, but prevented from axial movement along the shaft. The distal head 53 includes an axial cylindrical surface 55 which is rotatable over a corresponding surface 56 on an adjacent support piece 57 to provide, with its journaled connection on the shaft, a universal movement of the head 53. A distal wing nut 54 is threaded on the shaft 41 between the distal stop nut 43 and the support piece 57 and can be turned manually to press the surfaces 55 and 56 together to lock the position of the distal head 53 in a selected position. The skeletal distraction 38 described therefore is of a construction known in the art.

Each of the proximal and distal heads 44 and 53, respectively, includes a pair of lateral through bores comprising a relatively large bore 58 and a smaller bore 60. Each of the large bores 58 is adapted to receive and support a threaded pin 61 which may be, for example, 3/16th inch in diameter. Correspondingly, each smooth bore 60 is adapted to receive and support a small pin 62 having a diameter, for example, of 7/64th inch. The small diameter smooth pins 62 are held against axial movement in their respective bores 60 by a suitable set screw 63.

To attach the first skeletal distractor 38, the proximal pin, either threaded 61 or smooth 62, is inserted in an approximately sized hole drilled laterally into the lower end of the tibia unicortically, generally perpendicular thereto, and about 1¾ to 2 inches above the ankle joint. If dual skeletal distraction is required, as will be discussed hereinafter, bicortical through penetration of the tibia is required so that a pair of distractors may be attached to opposite ends of a common pin. The distal pin is similarly inserted into a hole drilled laterally into (or through for bilateral distraction) the heel bone. One of three alternate insertion sites may be utilized depending on the required procedure. Two sites are in the calcaneus and one is in the talus. If single skeletal distraction with threaded 3/16 inch pins is utilized, the distal pin is preferably angled downwardly toward the heel bone, for example, 15° to 25° when utilizing calcaneal sites and depending on whether the attachment is lateral or medial, and angled downwardly only a few degrees if the pin is inserted into the talus. In this manner, the proximal and distal pins will assume a near parallel position at the point of maximum distraction as a result of slight rotation of the distal head 53 on its cylindrical surface 55. If dual bilateral distraction is utilized, of course, bicortical pin placement should be generally perpendicular to the bone and parallel to the proximal pin.

The smaller diameter smooth pins 62 are utilized if they provide enough support for the needed distraction. The larger diameter threaded pins 61 may be required for larger distraction forces. When using threaded pins 61, the distal pin, when initially inserted into the heel bone at a downward angle, is secured in the distal head 53 with a lock nut 59 to prevent the distractor from sliding off the pin before parallel pin orientation is achieved. In bicortical double distraction procedures, small diameter smooth pins are preferred, but the larger threaded pins may also be utilized. After the proximal and distal pins are in place, the distractor is attached to the pin ends and the wing nut 46 turned by hand to move the proximal head 44 axially away from the distal head 53. Relative movement between the distractor heads will be accompanied by distraction of the joint and movement of the load indicating pin 51 on the extensiometer 45.

Any one of the invasive techniques utilizing pinned connections results in the creation of a stress riser at the site of the drilled hole. Stress risers are, of course, doubled as the size of the hole as the pin holes change from unicortical to bicortical. The system of the present invention allows the surgeon to proceed initially with distraction means involving the least overall risk and proceeding, if necessary, to those providing higher distraction forces but involving greater overall risk.

Figure 9:
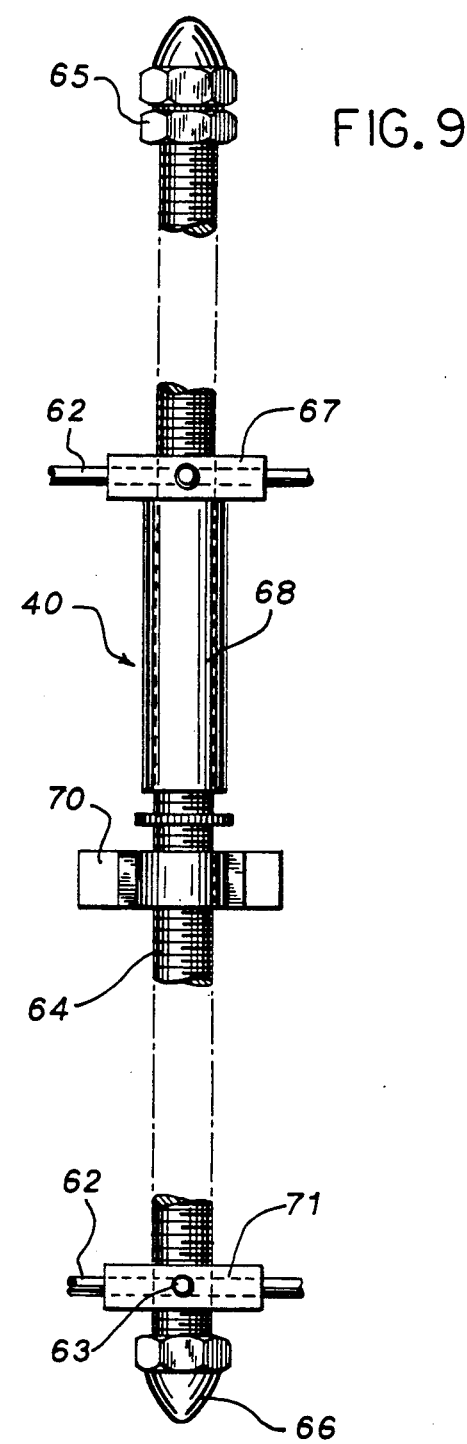
FIG. 9 is a side elevation of the second skeletal distractor, shown attached to the patient with the first distractor in FIG. 5.

If bilateral skeletal distraction is indicated, the second skeletal distractor 40, shown in FIGS. 5 and 9, may be installed along with a previously attached first skeletal distractor 38. A lower level of double distraction is provided by utilizing bicortically inserted smooth pins 62. The amount of distraction may be judged by reading the force on the extensiometer 45, as well as by noting the amount of bending occurring in the pins 62 and by arthroscopic viewing of the actual opening in the joint. If the smaller diameter smooth pins are not adequate to transmit sufficient distraction force, the surgeon may switch to the larger diameter threaded pins 61 which are inserted in the original smooth pin holes after the same are removed. Avoiding drilling an additional hole or holes eliminates the undesirable creation of a second stress riser.

The second skeletal distractor 40 is constructed in a manner similar to the first distractor 38, except that the extensiometer may be omitted and the distal head need not be attached for universal pivotal movement. Thus, the second distractor 40 includes a long threaded shaft 64 having proximal and distal stop nuts 65 and 66, respectively, attached to opposite ends thereof. A proximal head 67 may be identical to head 44 of distractor 38 and has integrally attached thereto a cylindrical sleeve 68 mounted to slide along the shaft 64. An adjusting wing nut 70 is threaded on shaft 64 and bears against the free end of the cylindrical sleeve 68 to move the proximal head 67 axially to provide extension of the distractor. A distal head 71 is secured to the opposite end of the shaft 64 by the distal stop nut 66. The distal head 71 need not be attached for rotation in either of the planes of rotation provided by the distal head 53 of the first skeletal distractor 38.

When bilateral skeletal distraction is used, the extensiometer 45 on the first (primary) distractor 38 is used to monitor distraction, along with observing pin binding and utilizing arthroscopic viewing. The first distractor 38 is the lead device and extension of the second skeletal distractor 40 should lag behind by a few turns.

Referring again to FIG. 4, either primary distractor 38 or both skeletal distractors 38 and 40 may be attached and operated with the leg supported only by the leg holder 12. In some cases, however, it may be desirable to provide an auxiliary ankle holder 72 during the surgical procedure. The ankle holder includes a foot piece 73. An ankle holder arm 74 is attached with a universal swiveling connection to the underside of the foot piece 73 and the lower end of the arm 74 is adjustable clamped in the clamp 24 on a Clark rail 13 over sterile drapes alternately used to support the distal end of the non-invasive distractor 18. The leg holder 12 may be adjusted to provide a wide range of flection of the knee joint to accommodate variable angular positioning of the lower leg and ankle, in the same manner described with respect to the non-invasive distractor 18 in FIGS. 1 and 3.

The system and related method of the present invention provide a combination of all the best features of both non-invasive and invasive distraction techniques which allows the surgeon to rapidly convert from one technique to another and reposition the angle at which the ankle is disposed during any technique, all with no loss of time, need to change the position of the patient on the operating table, or to reprep or to redrape the patient.

Various modes of carrying out the present invention are contemplated as being within the scope of the following claims particularly pointing out and distinctly claiming the subject matter which is regarded as the invention.

I claim:

1. A distraction system for ankle arthroscopy comprising in combination:
   means for supporting a patient in a generally supine position;
   means for adjustably supporting the leg of the patient posteriorly of the knee joint to maintain the leg in a selected position between slightly flexed and acutely flexed said leg supporting means attached directly to the patient supporting means below the knee;
   non-invasive distraction means including a first end adapted to be attached to the foot of the patient and a second end adjustably attached to said patient supporting means for providing a selectively variable tensile force on the ankle joint sufficient to provide an initial level of ankle joint distraction force, said second end being attached to said patient supporting means independently of said leg supporting means and spaced from the bottom of the foot of the patient in a direction generally axially of the lower leg, such that the entire area surrounding the ankle is unobstructed for substantially unrestricted access thereto; and,
   skeletal distraction means having a proximal end adapted to be pinned to the lower tibia of the leg and a distal end adapted to be pinned to the heel bone for providing a selectively variable tensile force on the ankle joint sufficient to provide a greater level of ankle joint distraction force than said non-invasive means, said skeletal distraction means attachable directly in said unobstructed area.

2. The system as set forth in claim 1 wherein said non-invasive distraction means comprises:
   an elongate body having an axially adjustable length and including said first and second ends;
   adjustment means operatively attached to said body for manually changing the length thereof;
   first connection means on said first end of said body for connecting said first end to the foot; and,
   second connection means on said second end of said body for connecting said second end to said patient supporting means.

3. The system as set forth in claim 2 wherein said adjustment means is operable to shorten the length of said body between said first and second connection means to provide said initial level of distraction force.

4. The system as set forth in claim 3 including first indicating means on said body for showing the magnitude of the tensile force.

5. The system as set forth in claim 4 wherein said non-invasive distraction means further comprises:
   a foot strap attached to said body by said first connection means; and,
   means for demountably attaching said foot strap to the foot.

6. The system as set forth in claim 5 wherein said patient supporting means comprises an operating table having a Clark rail attached to one edge thereof, and wherein said second connection means includes a clamp adjustably attached to said Clark rail.

7. The system as set forth in claim 1 wherein said skeletal distraction means comprises a first unilaterally attachable distractor having pin-supporting heads on its proximal and distal ends, each of said pin-supporting heads adapted to support a large diameter pin and a small diameter pin.

8. The system as set forth in claim 7 wherein said large diameter pin is threaded and said small diameter pin is smooth.

9. The system as set forth in claim 8 including a second unilaterally attachable distractor adapted to be attached opposite said first distractor and to share common bicortical proximal and distal pins therewith.

10. The system as set forth in claim 9 wherein said first distractor includes indicating means for showing the magnitude of the tensile force.

11. The system as set forth in claim 9 including means for adjustably supporting the foot during use of said skeletal distraction means.

12. The system as set forth in claim 11 wherein said foot supporting means comprises:
    a foot piece demountably attachable to the foot; and,
    a holder arm having a pivotal connection at one end to said foot piece and a pivotal connection at the other end to said patient supporting means.

13. The system as set forth in claim 9 wherein said second unilaterally attachable distractor includes pin-supporting heads on its proximal and distal ends, each of said heads adapted to operatively receive the opposite end of a pin from said first distractor.

14. A method for providing ankle joint distraction to facilitate ankle arthroscopy, said method comprising the steps of:
    (1) supporting the patient in a generally supine position;
    (2) adjustably positioning a leg of the patient to selectively maintain the leg between slightly flexed and acutely flexed positions by supporting the leg with a support beneath the knee joint;
    (3) applying a first selectively variable tensile force on the ankle joint sufficient to provide an initial level of joint distraction by externally applying a load on the foot of the patient generally axially of the lower leg and against the resistance provided by the leg support;
    (4) maintaining the entire area surrounding the ankle unobstructed while applying said first tensile force;
    (5) determining the sufficiency of the initial level of distraction; and,
    (6) applying, if necessary, a second selectively variable tensile force on the ankle joint sufficient to provide a greater level of joint distraction by skeletally applying a unilateral load between a proximal pinned connection in the lower tibia an da distal pinned connection in the heel bone, while maintaining the leg support beneath the knee.

15. The method as set forth in claim 14 including the step of applying, if necessary, a supplemental second tensile force on the ankle joint by:
(1) extending said pinned connections bicortically to the side of the ankle joint opposite the application of said unilateral load; and,
(2) skeletally applying a supplemental load between the extended pin connection concurrently with step (5).

16. The method as set forth in claim 14 including the steps of:
(1) continuously monitoring the externally applied load; and,
(2) continuously monitoring, if applied, the skeletally applied unilateral load.

17. The method as set forth in claim 14 including the step of adjustably supporting the foot during step (5).

* * * * *